（12）United States Patent
Sabel

(10) Patent No.: US 7,753,524 B2
(45) Date of Patent: Jul. 13, 2010

(54) PROCESS AND DEVICE FOR TREATING BLIND REGIONS OF THE VISUAL FIELD

(75) Inventor: Bernhard Sabel, Berlin (DE)

(73) Assignee: NovaVision, Inc., Boca Raton, FL (US)

( * ) Notice: Subject to any disclaimer, the term of this patent is extended or adjusted under 35 U.S.C. 154(b) by 0 days.

(21) Appl. No.: 11/669,783

(22) Filed: Jan. 31, 2007

(65) Prior Publication Data

US 2007/0182928 A1 Aug. 9, 2007

Related U.S. Application Data

(63) Continuation-in-part of application No. 10/503,869, filed as application No. PCT/EP02/01339 on Feb. 8, 2002.

(60) Provisional application No. 60/763,589, filed on Jan. 31, 2006.

(51) Int. Cl.
*A61B 3/02* (2006.01)
*A61B 3/10* (2006.01)
*A61B 18/18* (2006.01)
*A61N 5/06* (2006.01)

(52) U.S. Cl. .................. 351/224; 351/212; 607/88; 606/2

(58) Field of Classification Search .......... 351/212, 351/214, 216, 220, 222, 224; 607/87–88; 606/2
See application file for complete search history.

(56) References Cited

U.S. PATENT DOCUMENTS

| 1,463,847 | A |   | 8/1923  | Shilling |            |
|-----------|---|---|---------|----------|------------|
| 2,213,484 | A |   | 9/1940  | Briggs   | 128/76.5   |
| 3,883,234 | A | * | 5/1975  | Lynn et al. | 351/224 |
| 4,260,227 | A |   | 4/1981  | Munnerlyn et al. | 351/24 |
| 4,408,846 | A |   | 10/1983 | Balliet  | 351/203    |
| 4,421,392 | A |   | 12/1983 | Pitts Crick et al. | 351/224 |
| 4,429,961 | A |   | 2/1984  | Sheingorn | 351/226   |
| 4,533,221 | A |   | 8/1985  | Trachtman | 351/203   |

(Continued)

FOREIGN PATENT DOCUMENTS

DE 9305147 4/1994

(Continued)

OTHER PUBLICATIONS

Portable Tech/Emory Device Checks for Concussions, http://www.gatech.edu/news-room/release.php?id=554, Apr. 26, 2005.

(Continued)

*Primary Examiner*—Scott J Sugarman
*Assistant Examiner*—Dawayne A Pinkney
(74) *Attorney, Agent, or Firm*—Sunstein Kann Murphy & Timbers LLP

(57) ABSTRACT

A device and method are provided for treating the visual system of a human including the retina, visual cortex and/or other neuro-cellular structures. The method includes the steps of locating and defining a blind zone of deteriorated vision within the human's visual system, defining a treatment area which is located predominantly within the blind zone, and treating the human's visual system by presenting visual stimuli to the human's visual system. The majority of the visual stimuli are presented to at least a portion of the blind zone.

1 Claim, 11 Drawing Sheets

U.S. PATENT DOCUMENTS

| | | | |
|---|---|---|---|
| 4,660,945 A | 4/1987 | Trachtman | 351/203 |
| 4,679,920 A | 7/1987 | Takashi et al. | 351/226 |
| 4,971,434 A | 11/1990 | Ball | 351/224 |
| 4,995,717 A | 2/1991 | Damato | 351/224 |
| 5,035,500 A | 7/1991 | Rorabaugh et al. | 351/226 |
| 5,050,982 A | 9/1991 | Meissner | 351/203 |
| 5,088,810 A | 2/1992 | Galanter et al. | 351/203 |
| 5,139,323 A * | 8/1992 | Schillo | 351/45 |
| 5,147,284 A | 9/1992 | Federov et al. | 600/9 |
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,539,482 A | 7/1996 | James et al. | 351/246 |
| 5,550,602 A | 8/1996 | Braeuning | 351/243 |
| 5,565,949 A | 10/1996 | Kasha, Jr. | 351/224 |
| 5,883,692 A | 3/1999 | Agonis et al. | 351/224 |
| 5,886,770 A | 3/1999 | Damato | 351/237 |
| 5,912,723 A | 6/1999 | Maddess | 351/246 |
| 5,946,075 A | 8/1999 | Horn | 351/246 |
| 5,991,085 A | 11/1999 | Rallison et al. | 359/630 |
| 6,062,687 A | 5/2000 | Lofgren-Nisser | 351/46 |
| 6,286,960 B1 | 9/2001 | Tomita | 351/245 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,386,706 B1 | 5/2002 | McClure et al. | 351/237 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 * | 10/2002 | Sabel et al. | 351/203 |
| 6,519,703 B1 | 2/2003 | Joyce | 713/201 |
| 6,540,355 B1 | 4/2003 | Couture | 351/203 |
| 6,578,966 B2 | 6/2003 | Fink et al. | 351/239 |
| 6,592,221 B1 | 7/2003 | Stregova | 351/203 |
| 6,656,131 B2 | 12/2003 | Alster et al. | 600/558 |
| 6,688,746 B2 | 2/2004 | Malov | 351/239 |
| 6,742,892 B2 | 6/2004 | Liberman | 351/203 |
| 6,769,770 B2 | 8/2004 | Fink et al. | 351/239 |
| 6,990,377 B2 | 1/2006 | Gliner | 607/54 |
| 7,004,912 B2 | 2/2006 | Polat | 600/558 |
| 7,104,659 B2 | 9/2006 | Grier et al. | 359/614 |
| 7,220,000 B2 | 5/2007 | Alster et al. | 351/224 |
| 7,275,830 B2 | 10/2007 | Alster et al. | 351/223 |
| 7,309,128 B2 | 12/2007 | Cappo et al. | 351/224 |
| 7,367,671 B2 | 5/2008 | Sabel | 351/203 |
| 2002/0024634 A1 | 2/2002 | Fink et al. | 351/237 |
| 2002/0047987 A1 | 4/2002 | Massengill et al. | 351/204 |
| 2002/0107960 A1 | 8/2002 | Wetherall et al. | 709/225 |
| 2002/0186179 A1 | 12/2002 | Knowles | 345/8 |
| 2003/0020873 A1 | 1/2003 | Fink et al. | 351/200 |
| 2003/0090439 A1 | 5/2003 | Spitzer et al. | 345/8 |
| 2003/0156254 A1 | 8/2003 | Turovetsky | 351/203 |
| 2003/0214630 A1 | 11/2003 | Winterbotham | 351/203 |
| 2004/0012758 A1 | 1/2004 | Lin | 351/203 |
| 2004/0046934 A1 * | 3/2004 | Sponsel et al. | 351/200 |
| 2004/0051848 A1 | 3/2004 | Gotze et al. | 351/203 |
| 2004/0075811 A1 | 4/2004 | Liberman | 351/203 |
| 2004/0100616 A1 | 5/2004 | Eremeev | 351/203 |
| 2004/0257528 A1 | 12/2004 | Miyake et al. | 351/203 |
| 2005/0001980 A1 | 1/2005 | Spector | 351/203 |
| 2005/0004624 A1 | 1/2005 | Gliner et al. | 607/54 |
| 2005/0041208 A1 | 2/2005 | Winterbotham | 351/203 |
| 2005/0122477 A1 | 6/2005 | Alster et al. | 351/237 |
| 2005/0213033 A1 | 9/2005 | Sabel | 351/203 |
| 2005/0213034 A1 | 9/2005 | Nagayoshi | 351/203 |
| 2005/0213035 A1 | 9/2005 | Yoshimeki et al. | 351/203 |
| 2006/0092377 A1 | 5/2006 | Sabel et al. | 128/898 |
| 2006/0283466 A1 | 12/2006 | Sabel | 128/898 |
| 2006/0288258 A1 | 12/2006 | Lo et al. | 714/46 |
| 2006/0290885 A1 | 12/2006 | Covannon et al. | 351/212 |
| 2007/0038142 A1 | 2/2007 | Todd et al. | 600/558 |
| 2007/0121070 A1 | 5/2007 | Alster et al. | 351/224 |
| 2007/0171372 A1 | 7/2007 | Seal et al. | 351/245 |
| 2007/0182928 A1 | 8/2007 | Sabel | 351/224 |
| 2007/0216865 A1 | 9/2007 | Sabel et al. | 351/203 |
| 2008/0013047 A1 | 1/2008 | Todd et al. | 351/203 |
| 2008/0024724 A1 | 1/2008 | Todd | 351/222 |
| 2008/0043201 A1 | 2/2008 | Todd | 351/222 |
| 2008/0077437 A1 | 3/2008 | Mehta et al. | 705/2 |

FOREIGN PATENT DOCUMENTS

| | | |
|---|---|---|
| DE | 10207839 | 9/2002 |
| EP | 115263 | 8/1984 |
| EP | 128783 | 12/1984 |
| EP | 135736 | 8/1985 |
| EP | 0242723 | 10/1987 |
| EP | 0537945 A1 | 4/1993 |
| EP | 544631 | 6/1993 |
| EP | 689822 | 1/1996 |
| EP | 775464 | 5/1997 |
| EP | 830839 | 3/1998 |
| EP | 1107721 A1 * | 6/2001 |
| EP | 1186271 | 3/2002 |
| EP | 1236432 | 9/2002 |
| EP | 1236433 | 9/2002 |
| EP | 1384462 | 1/2004 |
| EP | 1402869 | 3/2004 |
| EP | 1403680 A1 | 3/2004 |
| GB | 1465561 | 2/1977 |
| WO | WO 8000405 | 3/1980 |
| WO | WO 8810088 | 12/1988 |
| WO | WO 9100553 | 1/1991 |
| WO | WO 9110393 | 7/1991 |
| WO | WO 9200037 | 1/1992 |
| WO | WO 9517227 | 6/1995 |
| WO | WO 9700653 | 1/1997 |
| WO | WO 9811819 | 3/1998 |
| WO | WO 9849992 | 11/1998 |
| WO | WO 9952419 | 10/1999 |
| WO | WO 9959461 | 11/1999 |
| WO | WO 0012042 | 3/2000 |
| WO | WO 0036971 | 6/2000 |
| WO | WO 0113859 | 3/2001 |
| WO | WO 0145630 | 6/2001 |
| WO | WO 0147463 | 7/2001 |
| WO | WO 0180808 | 11/2001 |
| WO | WO 0209578 | 2/2002 |
| WO | WO 02/39754 A1 | 5/2002 |
| WO | WO 0239754 | 5/2002 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |
| WO | WO 03065964 | 8/2003 |
| WO | WO 03092482 | 11/2003 |
| WO | WO 03092570 | 11/2003 |
| WO | WO 03098529 | 11/2003 |
| WO | WO 2004066900 | 8/2004 |
| WO | WO 2005004985 | 1/2005 |
| WO | WO 2005037177 | 4/2005 |
| WO | WO 2005044096 | 5/2005 |
| WO | WO 2005063153 | 7/2005 |
| WO | WO 2005092270 | 10/2005 |
| WO | WO 2005110326 | 11/2005 |

| WO | WO 2005122872 | 12/2005 |
| WO | WO 2006002070 | 1/2006 |
| WO | WO 2006006563 | 1/2006 |
| WO | WO 2007109724 | 9/2007 |
| WO | WO 2008/077440 A1 | 7/2008 |

OTHER PUBLICATIONS

Erich Kasten et al., Computer-based training for the treatment of partial blindness, Nature Medicine, vol. 4, No. 9, p. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, p. 192-194, 2003.

Walter Widdig et al., Repetitive visual stimulation: A neuropsychological approach to the treatment of cortical blindness, NeuroRehabilitation, vol. 18, p. 227-237, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; © 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, Issue 26, © 2000.

Teaching the brain to restore sight; Popular Mechanics, Jan. 18, 1999, Associated Press Newswires, © 1999.

Philip A. Schwartzkroin, Synaptic Plasticity: Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry (1979).

J. Zihl, et al., Restitution of visual field in patients with damage to the geniculostriate visual pathway; Zihl and von Cramon, Human Neurobiology (1982).

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness".

F. Schmielau, Restitution of visual function in cases of brain damaged patients: Efficacy of localization specific sensory and sensomotoric rehabilitation procedures. In "Psychologie in der Neurologie" [Psychology in Neurology], P. Jacobi (editor). Berlin: Springer, 115-126(1989).

E. Kasten et al., Restoration of vision II: Residual functions and training-induced visual field enlargement in brain-damaged patients. K.K. ball, et al, Journal of the Optical Society of America A, vol. 5, No. 12, pp. 2210-2219 "Age and Visual Search: Expanding the Useful Field of View", Dec. 1998.

E. Kasten, et al., Spatial Vision, vol. 10, No. 4, pp. 499-503, "Programs for Diagnosis and Therapy of Visual Field Deficits in Vision Rehabilitation", 1997.

E. Kasten, et al., Restorative Neurology and Neurology and Neuroscience, vol. 8, No. 3, pp. 113-127, "Visual Field Enlargement After Computer Training in Bran-damaged Patients Whit Homonymous Deficits: An Open Pilot Trial", Aug. 1995.

Alan Cowley, Perimetric Study of Field Defects in Monkeys After Cortical and Retinal Ablations, Quarterly Journal of Experimental Psychology, pp. 232-245, Dec. 18, 1967.

New Research on the Efficacy of NoveVision VRT Presented at 32nd Annual North American Neuro-Ophthalmology Society Meeting; Mar. 2, 2006, Business Wire © 2006.

Sharon Begley, Training the brain to see again; Sharon Begley, May 1, 2005, Saturday Evening Post, vol. 277; Issue 3; ISSN: 00489239; © 2005 Bell & Howell Information and Learning Company.

In-Sung Yoo, Advances in Medicine: New therapy gives hope to stroke victims; In-Sung Yoo, Mar. 1, 2005, The New Journal, © 2005, The New Journal.

Sharon Begley, Stroke patients have hope in sight; As part of the revolution in neurobiology, doctors are trying to train healthy brain cells to take over the visual function of neurons damaged by a stroke; Sharon Begley, Wall Street Journal, Feb. 4, 2005, The Globe and Mail.

John Dorschner, Stroke victims improve vision with computer therapy; John Dorschner, Knight Ridder Newspapers, Jul. 19, 2004, The Tallahassee Democrat, © 2004.

Sharon Begley, Survival of the Busiest—Parts of the Brain That Get Most Use Literally Expand And Rewire on Demand; Sharon Begley, Oct. 11, 2002, The Wall Street Journal, © 2002.

Patienteninformation Sehtherapie, Spectros, Nethera, http://www.teltra.org/cms/site/index.php?id=29, 2005.

Patienteninformation Sehtherapie, Otcb, Nethera, http://www.teltra.org/cms/site/index.php?id=11, 2005.

Spectros Technik/Ablauf, Nethera, Teltra, http://www.teltra.org/cms/site/index.php?id=77, 2005.

International Search Report.

* cited by examiner

F = Fixation Point
TS1 = Target Stimulus 1
VF = Visual Field
MF = Monitor Frame

I = Intact Visual Field Sector
FA = Fixation Anchors
MF = Monitor Frame
B = Blind Region
TS1 = Letters or Words as Target Stimuli
VF = Visual Field

PROCESS AND DEVICE FOR TREATING BLIND REGIONS OF THE VISUAL FIELD

CROSS REFERENCE TO RELATED APPLICATIONS

This application claims priority from U.S. Provisional Patent Application Ser. No. 60/763,589. filed Jan. 31, 2006. and is a continuation-in-part of U.S. patent application Ser. No. 10/503,869, filed May 18, 2005 in the United States, which claims priority from PCT Patent Application No. PCT/EPO2/01339, which was filed in English on Feb. 8, 2002; all of these applications are hereby incorporated by reference in their entirety.

TECHNICAL FIELD AND BACKGROUND ART

The present invention relates to treatment of the blind regions in a person's visual field.

Damage to the visual system, as used herein, is defined as impairment of any structure (or of all structures) involved in the processing of vision. These structures include, but are not restricted to, the nervous system tissue from the level of the retina, including the retina up to the optic nerve and all brain structures involved in visual processing. Such damage leads to deficits or even a loss of visual functions which may result in partial or more or less complete blindness. This damage may come from many sources and may include damage to the retina or damage to the visual cortex, specifically the primary visual cortex (V1). Damage to the visual system can be due to causes that include trauma, stroke, tumor growth or inflammatory diseases. The retina may also be damaged by retinal detachment, laser damage or other causes, such as glaucoma or age related macular degeneration. Damage to the retina shall be referred to herein as "retinopathies."

Perimetry methods (static or kinetic) systematically measure the visual field function of a subject and are used to identify regions of the visual field in which vision is normal, reduced, or absent (blind).

Treatment of a zone of deteriorated vision or residual visual function or partial visual system injury ("transition zone") has been taught in U.S. Pat. No. 6,464,356 and the treatment of zones of intact vision has been taught in U.S. patent application Ser. No. 10/503,869 (publication number 2005/0213033) both of which are incorporated herein by reference in their entirety.

The "blind zone," however, has not been considered amendable to remedial treatment. The reason for this was that once the visual cortex is damaged, the assumption was that no vision restoration is possible. However, in recent years several authors have described neuronal pathways in the brain which bypass the damaged cortex and are therefore often not affected by the injury. These are typically referred to as "extrastriate" pathways and permit information to travel from the retina to higher processing centers of the brain, thereby bypassing the primary visual cortex or other damaged regions.

In the normal brain these pathways are believed to be involved in the perception of moving visual stimuli and consequently, when the primary visual cortex is damaged, they still maintain the patients ability to see (or guess correctly) moving stimuli without the patient having a full awareness of the visual stimuli. This phenomenon is known as "blindsight".

It is a well recognized problem that patients with damage to the primary visual pathway can not see visual stimuli, thus having areas of complete or partial blindness. While current stimulative treatment paradigms may help regain some of the lost vision, the approach of this prior art is to stimulate areas of residual vision (ARVs) of the damaged primary pathway itself, where some residual vision can be found at the time of commencement of therapy. However, the progress achieved by stimulating surviving cells in the primary system is very labor intensive and may not achieve complete restoration. Therefore, methods are desirable whereby faster or more complete restoration may be achieved.

SUMMARY OF THE INVENTION

Embodiments of the present invention may speed up recovery of vision and restore vision to a greater extent than previously achieved. In some embodiments, stimulation paradigms which make use of the secondary, surviving visual pathway which still provides information to a blind zone may be implemented. This approach may more massively stimulate the areas higher up in the brain (beyond the primary visual cortex) and thus enhance the overall restoration of vision. The stimuli may be moving stimuli. The moving stimuli could be in the form of simple or more complex geometric figures or objects.

In a first embodiment of the invention a method for treating the visual system of a person is provided. At least one blind zone is located in patient's visual field. The method of this embodiment may include: presenting a stimulation pattern to the person in such a manner that it is presented to at least a portion of the at least one blind zone and recording responses of the person based on the stimuli. The method of this embodiment may also include presenting a further stimulation pattern based on the response. In an embodiment, the stimulation pattern is presented to the entire blind zone. In another embodiment, the majority of stimuli are presented to the blind zone.

Other embodiments of the present invention include a device or system that performs the steps described above. In an embodiment of the invention, a device is provided for treating a visual defect of a human. The device includes a light emitting module that has multiple separably actuatable locations, each location adapted to emit light stimuli so as to target a different region of the human's visual field. The device also includes a processor module that repeatedly selects and actuates the actuable locations based on an input visual field map of the human. The processor selects the majority of the actuable locations so as to target a blind region of the visual field.

In related embodiments, the device may include an input module for capturing responses of the human to the light stimuli. The processor may use these responses to selectively target the blind region. The processor may also select and actuate one or more fixation stimuli. The fixation stimuli may include multiple fixation anchor locations surrounding a central blind zone.

In other embodiments of the invention, a method is used to treat the visual system of a human including the retina, visual cortex and/or other neuro-cellular structures. A blind zone of deteriorated vision is located and defined within the human's visual system. A treatment area located predominantly within the blind zone is defined and visual stimuli are presented to the human's visual system. The majority of stimuli are presented in at least a portion of the blind zone.

The steps of locating, defining and treating the blind zone may be reiterated so as to extend the human's intact visual field into zones that were previously located and defined as transition or blind zones. A computer may be used to perform the steps in an automated or semi-automated manner. The reiteration may include stimulation directed to areas that are proximal to the borders of the blind region.

The steps of locating and defining the blind zone may be accomplished using perimetry. These steps may also be accomplished by automatically presenting stimuli to target multiple areas of the visual field and recording the human's response to the stimuli.

The stimuli used may be static or dynamic (moving) stimuli. The stimuli may be emitted from a head mounted display. The head mounted display may present a first stimulation series to a first eye of the human, and a second stimulation series to another eye of the human. If a blind zone is associated with the first eye, the second eye may be treated with a different stimulation regime. The different stimulation regime may target a transition zone, an intact zone, or no zone at all.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

The term "zone of intact vision" as used herein means a zone of the visual field (or brain area) which is substantially not injured or influenced by the events resulting in an impairment of the visual system, i.e. shows normal or negligibly deteriorated visual performance when receiving optical stimuli. In contrast, the term "zone of deteriorated vision" (which is used in a similar sense as the term "zone of residual visual function" or the term "zone of partial visual system injury") is defined to mean the zone where events like accidents, stroke, degenerative diseases, or retinal diseases such as glaucoma or retinitis pigmentosa caused damage of the brain regions or the retina influencing the visual capabilities of the human so that the vision is at least partly deteriorated or even partly or completely lost.

The invention relates, generally, to a process for treating the vision of a person by presenting optical stimuli to them. By stimulating the pathways that have survived injury using specific stimuli that address these pathways, vision restoration may be achieved in a more complete or faster manner. In illustrative embodiments, the stimuli are presented to a "blind zone" in the visual field of the person. The term "blind zone" as used herein means any zone of the visual field that would be classified as blind using routinely applied visual field testing methods (i.e., excluding extraordinary methods such as use of magnetic resonance imaging). In general, it is a zone of the visual field in which a person cannot consciously respond to stimuli presented by perimetric methods.

In embodiments of the present invention, treatment is effected by directing optical stimulation energy so as to predominantly target the blind zone of the person. In related embodiments, the stimulus is directed only to the blind zone of the person.

Figure 1:
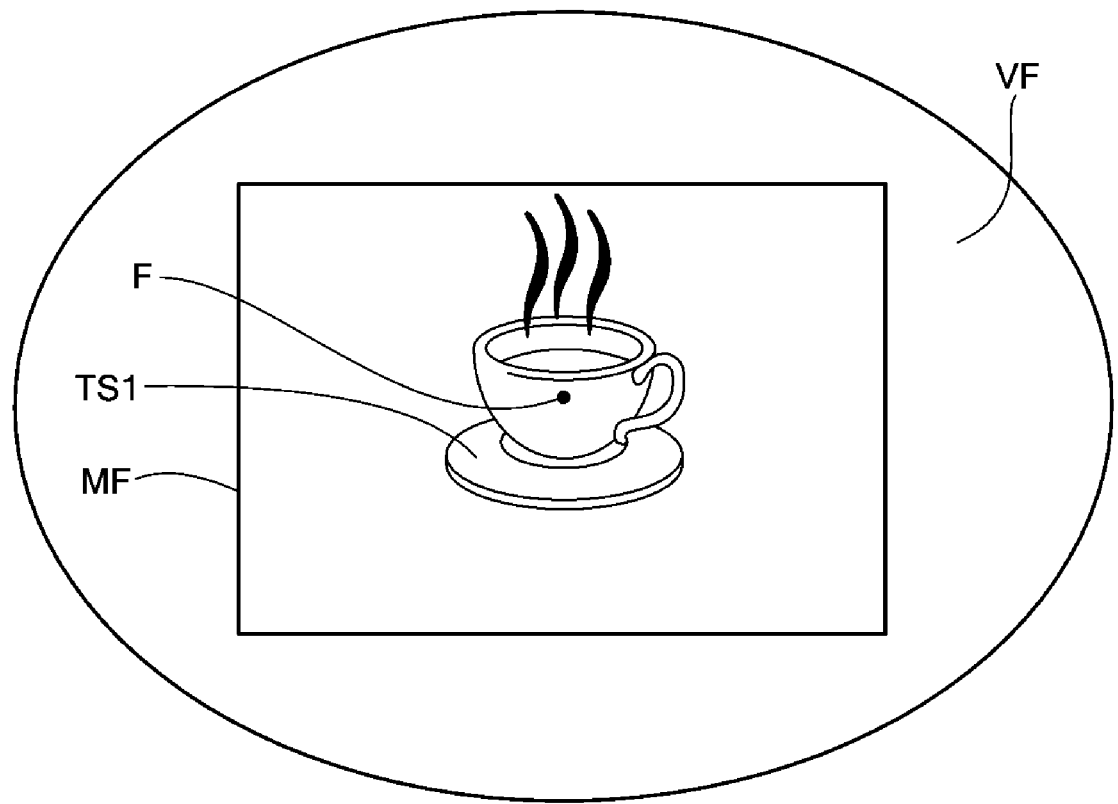
FIG. 1 represents vision in a normal visual field.

FIG. 1 shows a normal visual field (VF) defined to have a circular shape. A target stimulus TS1 is shown as being presented to the visual field VF on a monitor having a monitor frame (MF). The target stimulus TS1 may be presented, for example, on a computer monitor. The stimulus could be any type of a stimulus, and several or many stimuli may be presented together or successively with or without different types of background. Useful target stimuli could be, but are not limited to, letters, words, sentences, meaningful objects (drawings, faces, photographs etc.) or objects without meaning (dots, a line pattern etc.) moving or not moving on the screen. The stimulus may comprise a dynamic pattern of one of shapes, forms and colors. In addition, the presentation of the target stimulus could be varied in one more ways. For instance, one or more of the color, luminance, intensity, shape, or size of the stimulus may be varied as it is presented to the person.

The fixation point (F) for fixing the eyes of the person to be treated and the target stimulus may be presented in a location. As shown, the fixation point (F) is in the intact vision zone.

In some embodiments of the present invention, however, the presentation of the target stimulus TS1 (and thus the fixation point F) is occurring in or near the blind zone.

Figure 2:
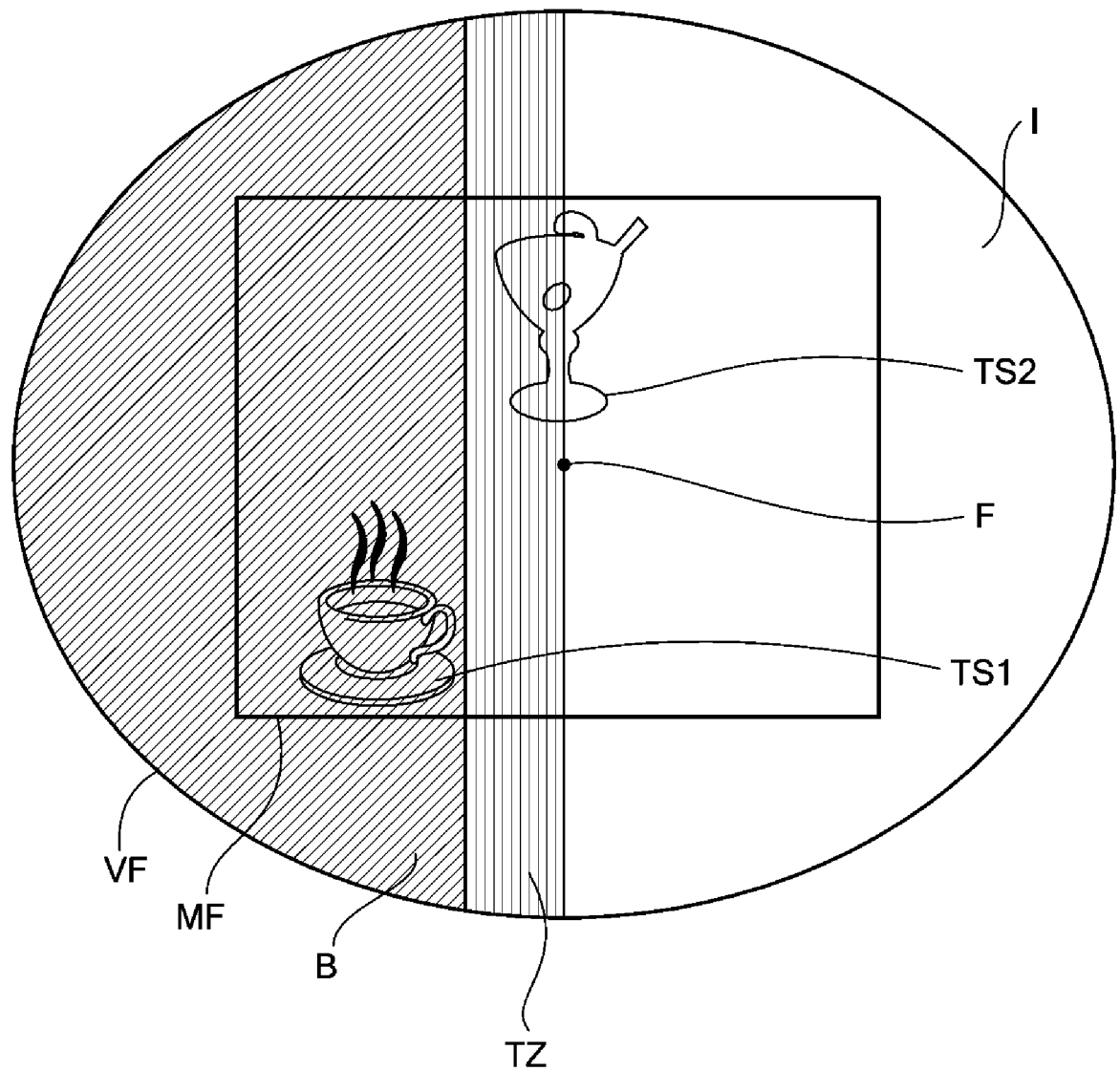
FIG. 2 represents a visual field where one hemisphere does not function.

FIG. 2 shows the case where the visual system in one hemisphere does not function. This hemisphere is the blind zone (B). In one embodiment, the fixation point F is presented in the blind zone, as is the target stimulus "TS1", i.e. the stimulus for treatment of the blind zone. As shown, and optionally, another target stimulus "TS2" may be presented partly in the intact and partly in the injured field (transition zone TZ).

Figure 3:
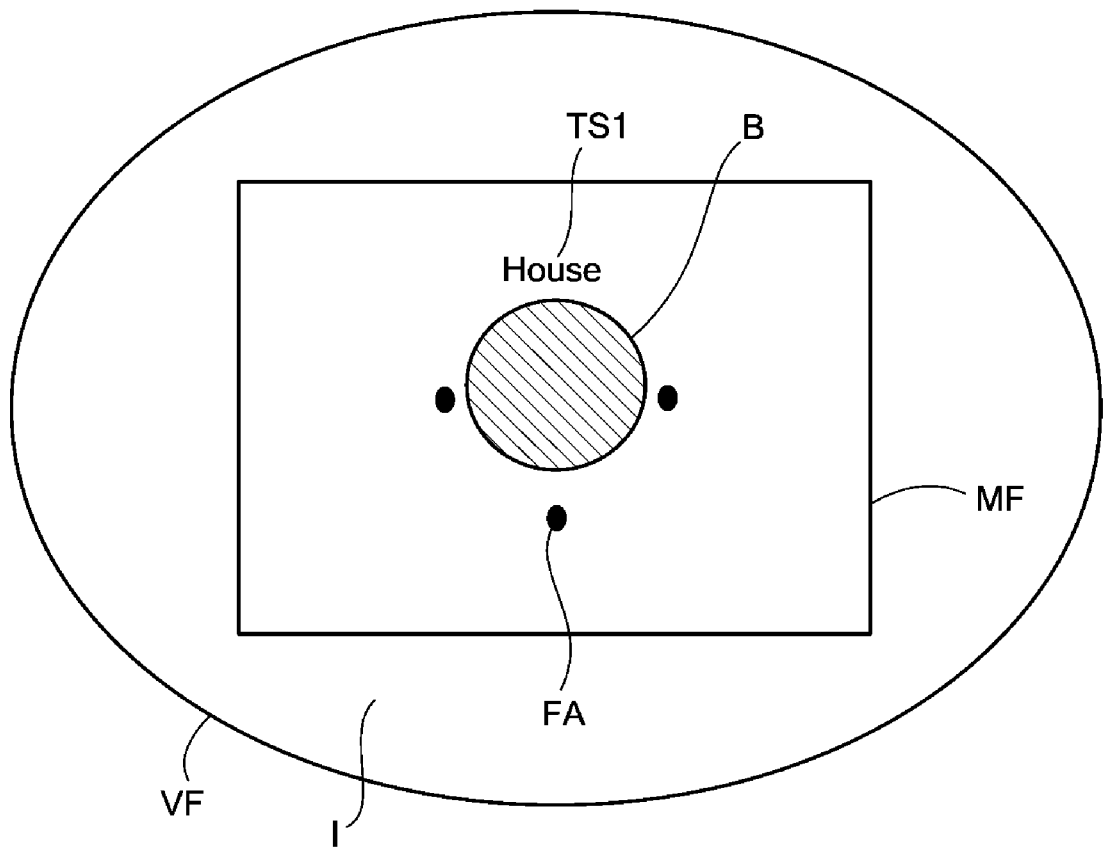
FIG. 3 represents a visual field where the central area of the visual field is injured.
Figure 4:
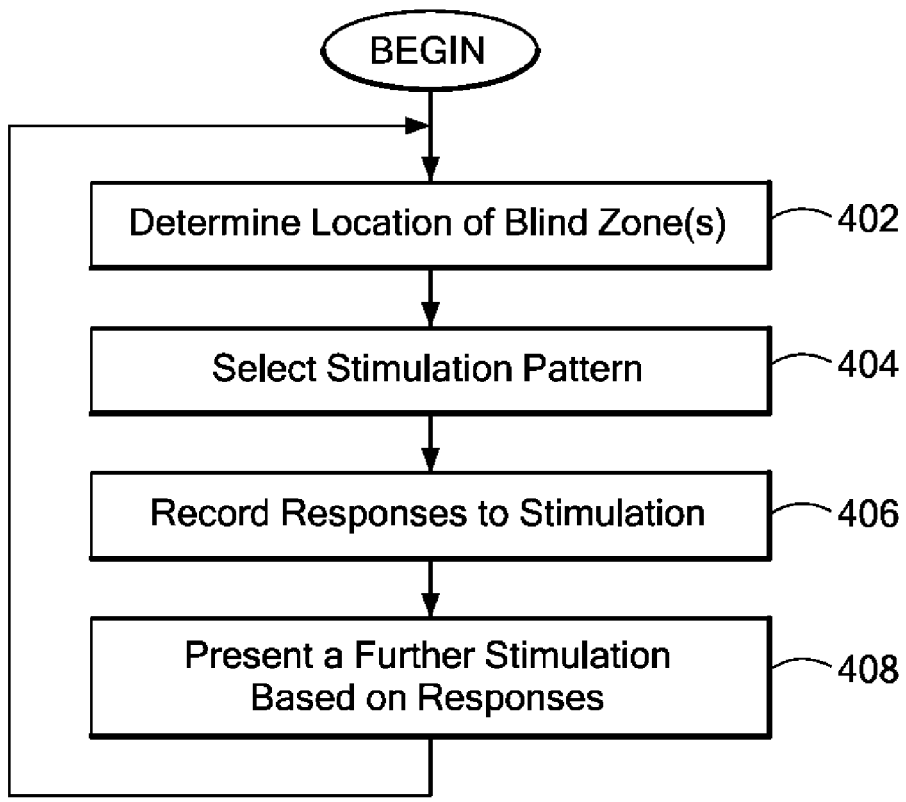
FIG. 4 shows one example of a method of treating a blind zone.

FIG. 3 shows the case where the central area of the visual system (e.g. where the fovea is located) is injured ("donut-shaped visual field"). In such a case, the fixation point cannot be presented in the central area (due to the injury, it would not be recognized), but so-called "fixation anchors" are presented in the peripheral part of the blind region where the intact vision zone is located and defined. Then, a visual stimulus is presented in the intact vision zone, in this case in the form of a word. The fixation stimuli may also be centrally located. By way of example, a fixation stimulus may be a change in color for 200 ms intervals. The color changes may be initiated at variable times so as not to be predictable by the patient. The patient is instructed to respond to the changes in fixation stimuli by pressing a button, the pressing of which is recorded by the processor. The fixation stimulus may be, for example, a 9 pixel green stimulus on an LCD display, that changes to a yellow stimulus after varying time intervals. The fixation stimulus may also be adapted to individual patients for example, making it larger, or using non-color shape cues for color-blind patients. In one embodiment, and as shown generally in the flow chart of FIG. 4, the location, and optionally the size, of the blind zones may be determined (step 402). In some embodiments, the location and size of the transition zones may be determined. The measurement may be done by methods known from the prior art. In one embodiment of the invention, standard perimetry devices may be used, i.e. those devices, which are commonly used in the ophthalmological practice.

In another embodiment, a computer-based campimetric measurement may be conducted that quantifies vision levels at various points within the perimeter of the visual field. With such a device, blind, partially injured and intact sectors of the visual field can be defined. In some embodiments, the treatment area may be selected in accordance with the size and location of the blind zone. In one embodiment the transition zones may be treated together with the blind zones.

A stimulation pattern is also selected (step 404). As discussed above, the stimulation pattern may be any stimulus at all. For example, a stimulus may be sized to stimulate the entire blind field without simultaneously stimulating the intact field. The stimulus may also be a moving stimulus (such as a moving spiral, gratings or moving forms and shapes). A computer screen, a VRT device, lenses or screens of a head mounted display (e.g., goggles) or glasses, or other suitable emissive device may be employed to present the stimulation pattern.

The response of the person to the stimulation may be recorded and may indicate a change in the visual system (step 406). That is, the person may indicate that a stimulus has been seen and the indication may be received. For instance, the person could press a button to indicate when the stimulus was seen. In some embodiments, such a stimulus may be detected even if the stimulus is presented to the blind zone. Optionally, the screen or the person may be masked so that the stimuli are only presented to the blind zones. The masking process may be done physically or, more conveniently, computationally.

Based on the individual person's performance, which may be determined continuously or intermittently during a treatment session, or between treatment sessions, stimuli may be presented to differing portions of the blind zones. The type, shape, intensity, duration and time sequence of the treatment stimuli is not restricted; one or more types of treatment stimuli may be used. In the latter case, several types may be used simultaneously or in a time sequence. In some embodiments of the invention, optical or light stimuli are presented to the person's visual system. In some embodiments, light stimuli of different colour, luminance, intensity and/or shape may be presented to the visual system of the person being treated. Such light stimuli can be presented as static light stimuli or a series of light stimuli in a sequence generating an impression of a moving object. In another embodiment, stimuli in the form of simple or more differentiated depictions of articles of daily life may be presented to the intact vision zone of the person to be treated. Such depictions may be static or moving (dynamic), according to the needs. The invention, however, is not at all restricted to the above preferred embodiments of stimuli to be presented.

Figure 5:
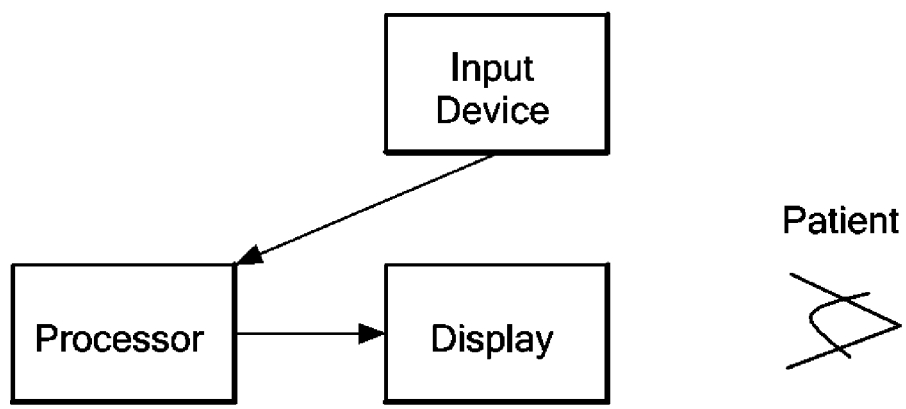
FIG. 5 shows a schematic plan for a device in accordance with an embodiment of the invention.

FIG. 5 shows a schematic diagram of a device for selecting a targeting parameter of a light stimulus, driving a light emitting display using the parameter to emit the stimulus, and recording the patient's response to the stimulus, and automatically using the patient's response to select a new parameter for repeating the process. The patient is positioned in a fixed position in front of the display. The computer selects a region of the display and drives the display to emit light in that region. The computer also emits fixation stimuli, e.g., the fixation anchors of FIG. 3. The patient inputs their response using the input device and the response or lack of response is recorded by the computer. After testing various regions of the patient's visual field, the computer uses the test information to adaptively select a different region to stimulate. The computer may be adapted to execute any of the therapeutic processes described herein. The display may be a desktop-type display such as an LCD or CRT. Processing circuitry may optionally be incorporated into the display. A head positioning device may be employed to reproducibly position the patient's head with respect to the desktop display. Alternately, the display may be a head-mounted display, e.g., goggles or a helmet with embedded display screens for each eye. If a head mounted display is used, different therapeutic regimes may be presented to each eye. For example, if one eye has a blind spot and the other eye has only lesser deterioration in vision, stimulation may be presented to the blind spot of the more affected eye and to transition regions of the lesser affected eye.

Figure 6A:
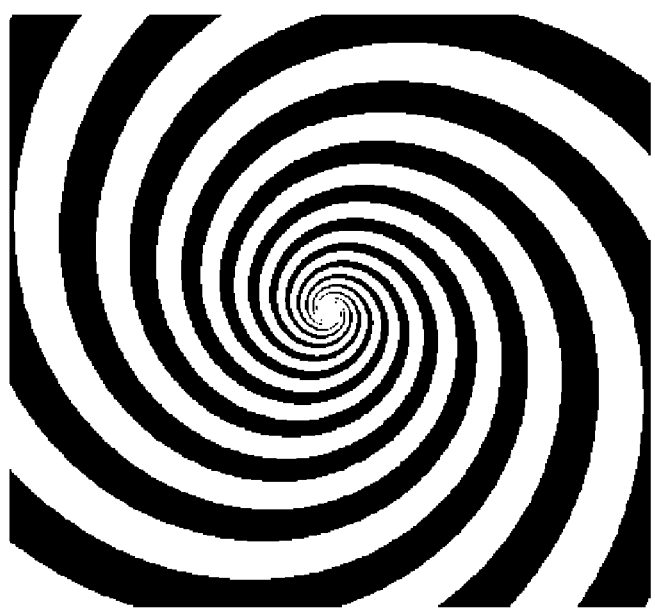
FIG. 6a shows a spiral stimulus.
Figure 6B:
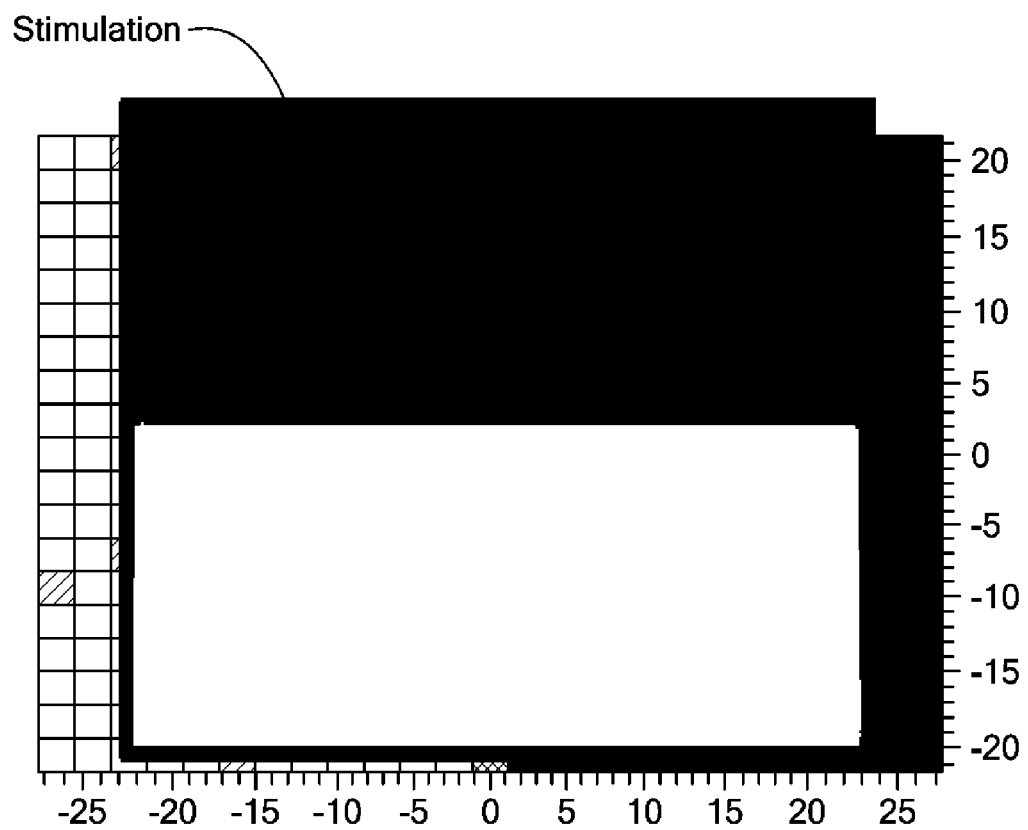
FIG. 6b shows a map of the spiral stimulus of FIG. 6a as it affects the visual field of a patient.
Figure 7A:
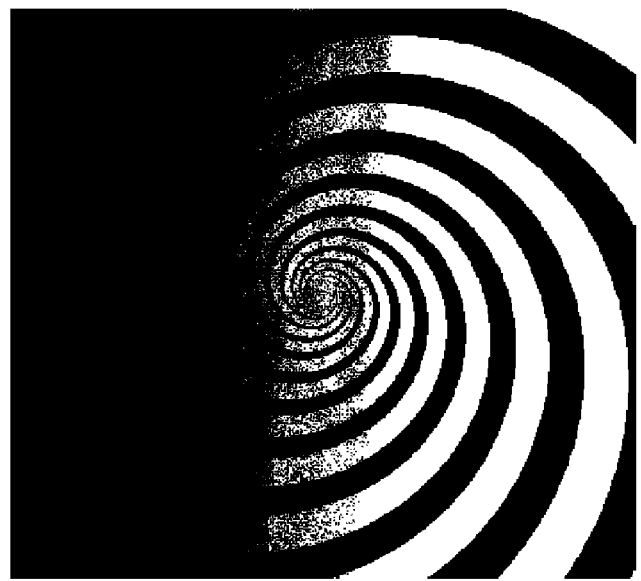
FIG. 7a shows a masked spiral stimulus.
Figure 7B:
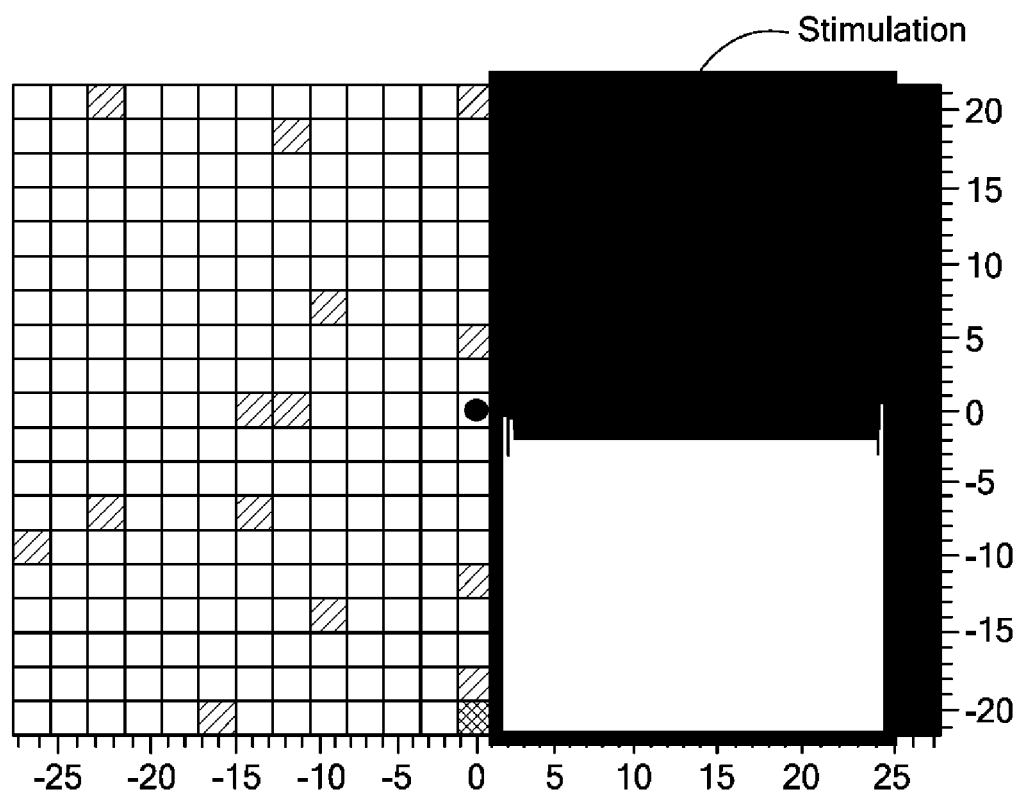
FIG. 7b shows how a masked spiral stimulus of FIG. 7b affects the visual field of a patient.

FIG. 6a depicts a moving spiral stimulus. However, if presented unchanged, the spiral will stimulate the intact field, as represented in FIG. 6b. This may be bothersome to patients because this stimulation dominates perception. To overcome this problem, the embodiment shown in FIG. 7a may be used; the spiral is not shown in full but is only limited to the blind field, as depicted in FIG. 7b. In the embodiments of FIG. 6a through 7b, the majority of the blind field is stimulated.

Figure 8:
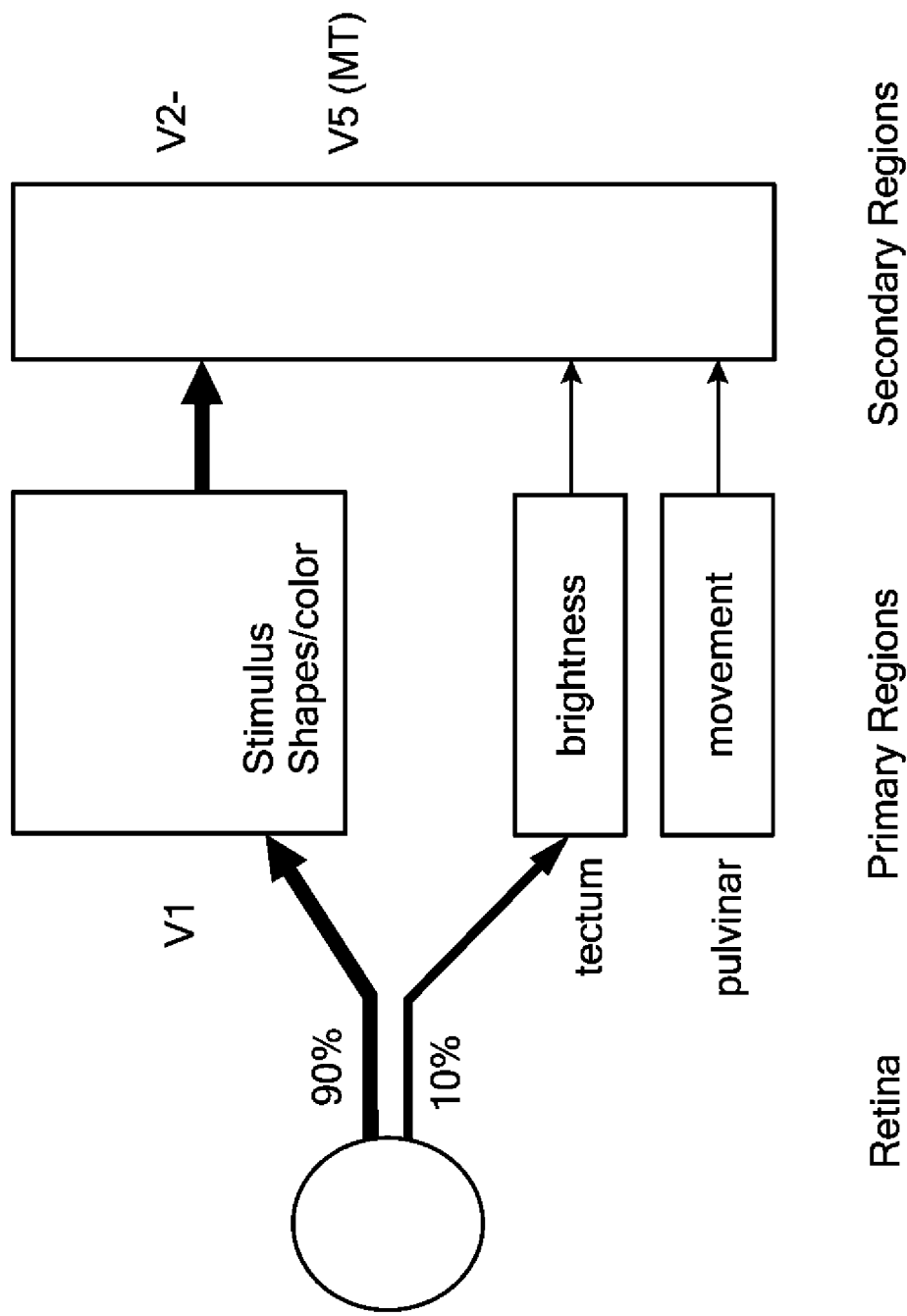
FIG. 8 shows a schematic diagram of the visual system.

FIG. 8 shows a schematic of the visual system. The circle on the left indicates a spot stimulus that has effects on two branches of the visual system: the primary regions (V1) and the higher, secondary cortical regions (V2-V5). The motion detecting pathway is indicated by "MT". The stimuli exerts approximately 90% of its effects on V1 and the remainder of its effects (about 10%) on the secondary regions. The existence of the secondary visual system beyond V1 consists of two extrastriate pathways and of two pathways in the visual extrastriate cortex. The extrastriate pathways run over tectum and pulvinar bypassing V1 and transfers information directly to higher extrastriate cortex areas.

Figure 9:
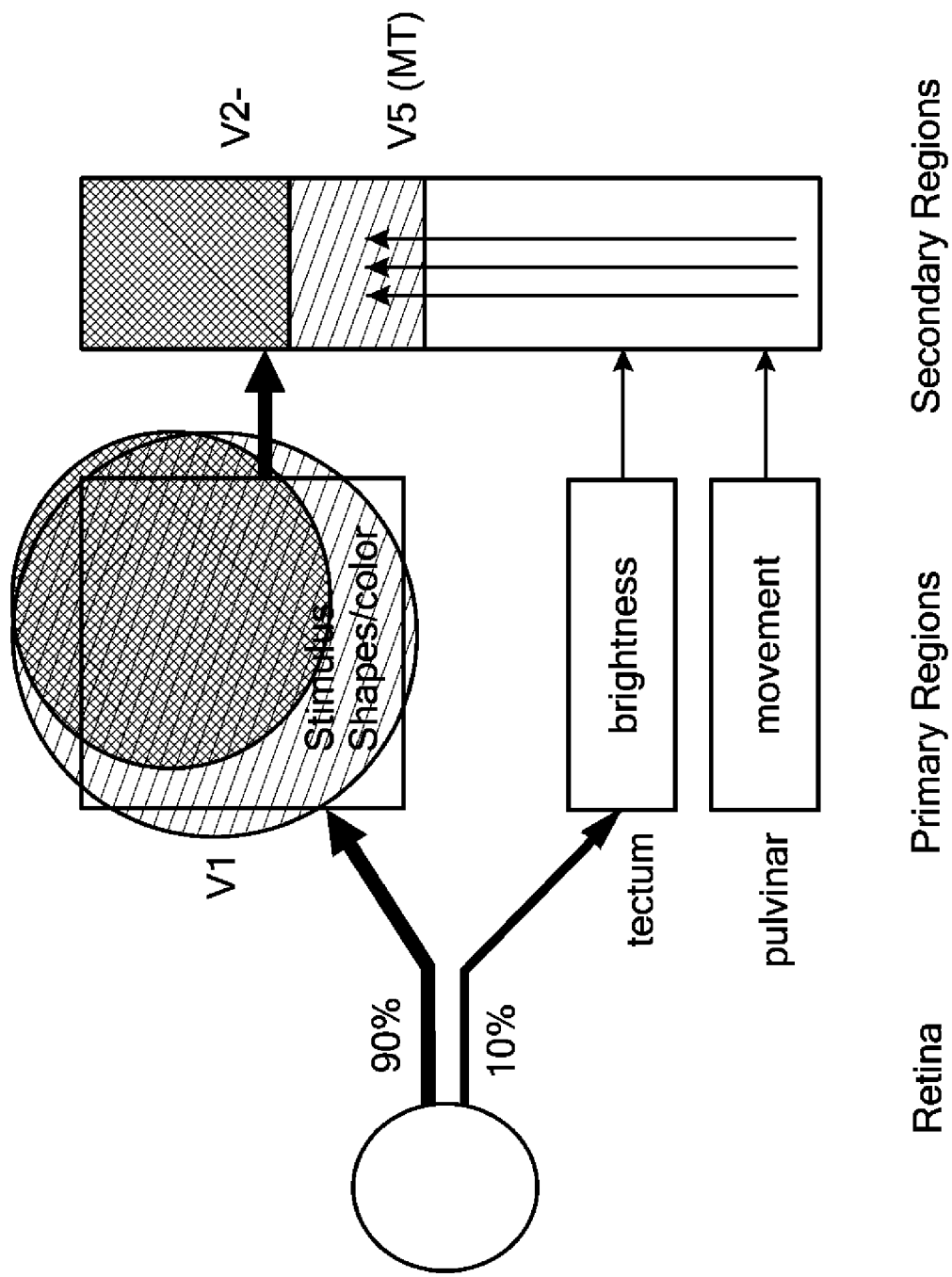
FIG. 9 shows a representation of the visual system with a lesion.

FIG. 9 shows the effects of a lesion on the primary and secondary visual system. The blind areas are presented by the black circle for V1, and by the black rectangle for the secondary system. The transition zones are represented as a speckled circle and rectangle respectively. If the damage is in V1, the higher cortical regions (V2-V5) will receive reduced input and may atrophy as a result.

Figure 10:
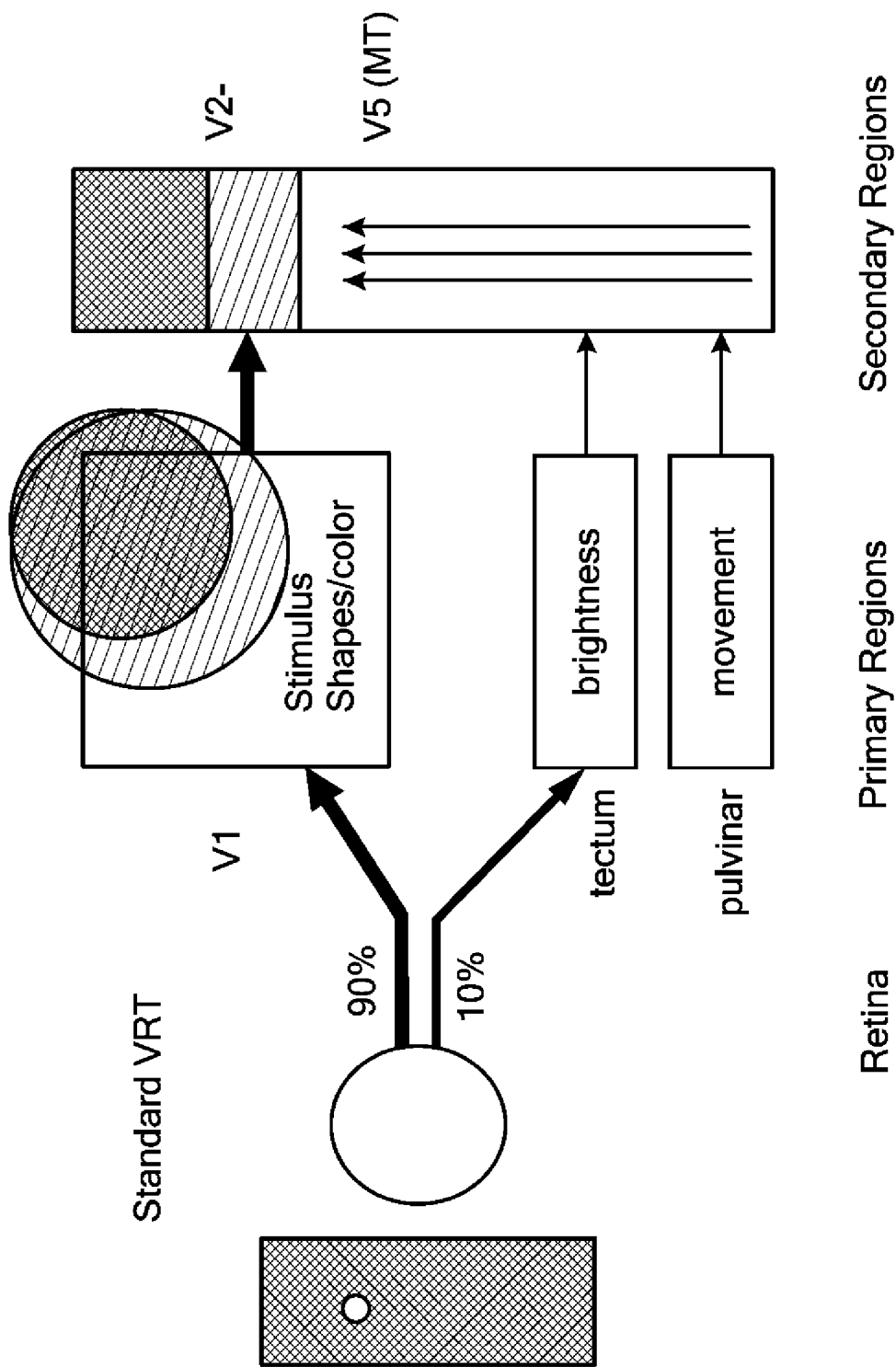
FIG. 10 shows how the visual system of FIG. 10 may be stimulated by conventional VRT.

FIG. 10 depicts the effects of standard VRT (i.e., Visual Restoration Therapy that does not primarily target the blind zones). The rectangle on the left hand side represents a dark display with a localized luminous stimulus shown as a white circle. The effects of VRT in shrinking the blind zone and transition zones are exerted primarily through V1.

Figure 11:
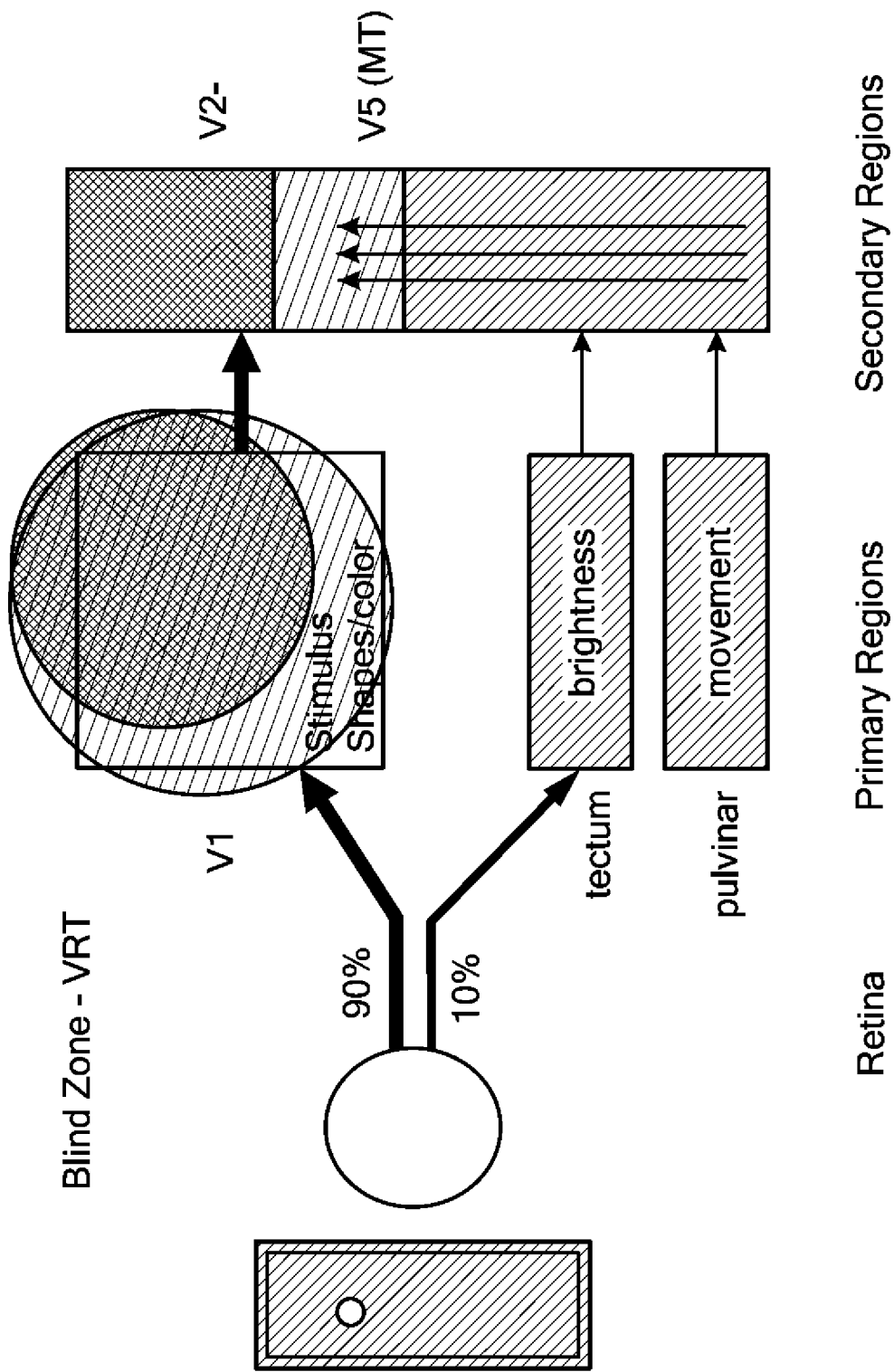
FIG. 11 shows how the visual system of FIG. 10 may be stimulated by embodiments to the present invention.
Figure 12:
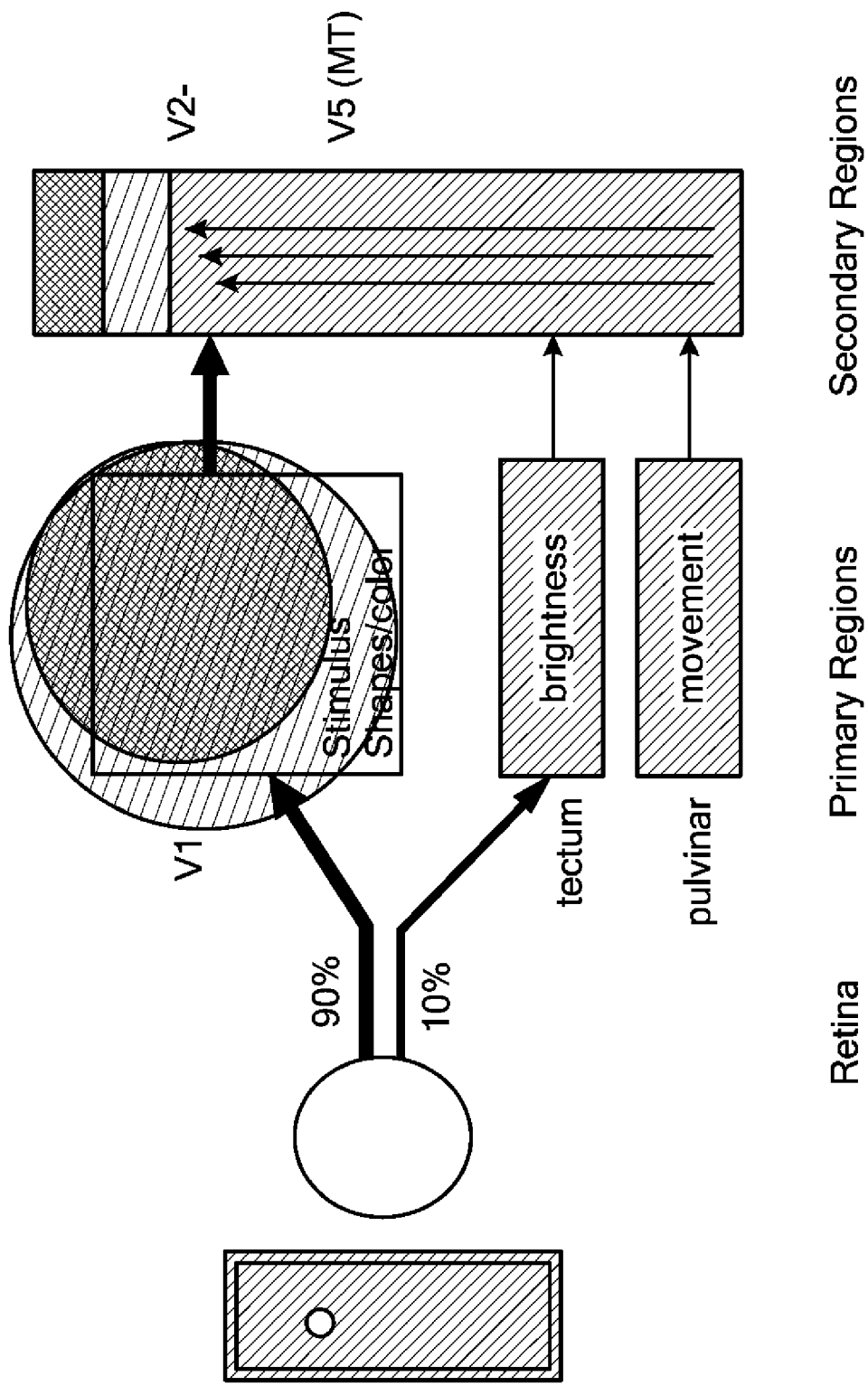
FIG. 12 shows how the visual system of FIG. 12 might improve as a result of embodiments of the present invention.

In contrast, FIG. 11 shows how an embodiment of the present invention (e.g., as described with respect to FIGS. 7a-7b) stimulate the tectum and pulvinar to excite the alternative paythway and thereby promote vision restoration. The rectangle on the left represents a moving spiral stimuli applied predominantly to the majority of the blind zone to target the secondary regions. Optionally, a highly luminous spot stimulus may be presented in a specific region of the moving stimulus to also target V1 and thereby effect both types of therapy, with potentially synergistic effects. FIG. 12 shows the potential results of such therapy in which the blind and transition zones associated with the secondary regions have been reduced in size, rendering the higher regions more responsive to stimuli through any of the routes.

In some embodiments, algorithms may be used to follow the above presentation strategy. Use of these algorithms allows highly efficient treatment of zones or areas of visual system function (and, optionally, also parallel or consecutive treatment of dysfunction or malfunction). The detailed steps of the treatment procedure are described below with respect to stimulating specific areas or zones of the human visual system by optical stimuli.

During the treatment step, changes in the characteristics of the visual system of the patient are recorded. In other words, the performance of the patient in visually recognizing and responding to the optical stimuli is recorded by the system/device of the present invention. To give an example, the reaction time of the patient to an optical stimulus presented to the intact zone of his/her visual system is measured. This reaction time may be compared to a reference value. The reference value may be a base-line value measured before the commencement of treatment. However, this example is not to be considered as limiting the invention; other measurement techniques may be used to continuously or intermittently record changes in the characteristics of the human's visual system.

In an embodiment, the reaction of the person to be treated upon the presentation of one or more stimuli is measured, and the performance of the person is rewarded. This may happen in a way that reward points are added to a "reward account" when the responses fulfill a predetermined criterion. For example, when the person to be treated is instructed to perform as fast as possible, reward points are added to the reward account only in those cases where the response is recorded within a predetermined time delay (reaction time). Alternatively, reward points could be assigned to the reward account when a discrimination is properly made (e.g. correct form; correct colour; time discrimination).

Based on the measurement and recording of the changes in the characteristics as described above, the location and definition of the blind zone may be redefined. In other words, depending upon the performance of the patient in processing the presented optical stimuli by the visual system, the blind zone is newly defined. This process of redefinition may also be conducted continuously or intermittently. In an embodiment of the invention, the number of reward points is used to determine when to automatically increase the difficulty of the next task. Without wanting to be bound by the explanation, it can be assumed that, due to the effective treatment of the defined blind zone, the vision of the treated person may be improved in the blind zone. For example, improvement may occur in a measure of function including peripheral vision, visual acuity, ability to discriminate between different colours, shapes, movement; reduction of squinting; increase of the visual angle, improving visual functions in general or removing partial visual system injuries. As a result thereof, the intact vision zone is enlarged (and the blind zone reduced) or at least improved with respect to its contribution to the person's vision. As found in practice, a patient experienced a subjective improvement in overall vision associated with better performance in the treatment. By reiterating the above-described steps, the human's intact visual field may be extended into zones that were previously located and defined to be transition zones.

Treatment may be carried out with a computer-based medical device for use at home where persons to be treated practices on a regular basis. In one embodiment daily treatment for 1 hr in a darkened room for an extended time period may be performed, as for example a 6-months period as employed in this test. However, other treatment periods may also prove efficacious.

One algorithm produces, on a display device, an emission of light stimuli effecting a repetitive visual stimulation of the blind zone. In a first step, the "blind zone" is located, defined and characterized, i.e. there occurs a determination of the exact visual function in said intact vision zone with respect to location, size and kind. Then, a treatment area is defined which is located within the blind zone. The treatment area is a region within the blind zone where a recovery of the neuronal structures of the person's visual system could be expected due to the results of the definition and characterization of the blind zone in the first step.

In a subsequent step, the blind zone is stimulated in a manner that is based on the performance determined in the first and second steps. Typically, when stimulating the blind zone, little or no stimulation is given to the intact zone. Also, unlike prior art devices in which the program only stores the data for a later analysis, the embodiments of the present invention include a computer program that adapts, on a continuous or intermittent basis, treatment algorithms to the visual system performance in or near the blind zones. The computer program can operate to adaptively adjust the pattern of stimulation automatically, i.e., without human intervention. The program may be locally associated with the device so that no transmission of the data to a remote location, e.g., over the internet, is necessary. This process of adaptation may be performed after each response is collected from the patient, after groups of responses are collected, or after a measurement, e.g. a perimetric or campimetric measurement, reaches a given level of statistical significance. The program may also operate in a semi-automated manner, for example automatically adapting for a duration and also occasionally or periodically submitting data to a caregiver for review.

In addition, daily therapy results can be stored on suitable storing media like a tape or a disc which permits monitoring of compliance and which allows the therapy strategy to be adapted to the progress of the person. These daily therapy results may also be transmitted (in real time or delayed) over the internet.

In alternative embodiments, the disclosed methods for vision therapy may be implemented as a computer program product for use with a computer system, including a computer-based medical device using appropriate algorithms. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network, including a local area network (LAN) or wide area network (WAN), over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over a network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although the above discussion disclosed various exemplary embodiments of the invention, it should be apparent that those skilled in the art can make various modifications that will achieve some of the advantages of the invention without departing from the true scope of the invention.

What is claimed is:

1. A method for treating the visual system of a human including the retina, visual cortex and/or other neuro-cellular structures, the method comprising treating the human's visual system by presenting visual stimuli to the human, the majority of the stimuli targeted so as to stimulate regions of the retina that are currently blind and to predominantly stimulate at least one of the human's tectum or pulvinar.

* * * * *